United States Patent
Gause

(10) Patent No.: US 6,669,676 B1
(45) Date of Patent: Dec. 30, 2003

(54) HYGIENE ARTICLE HAVING AN INDIVIDUAL WRAPPING

(75) Inventor: Enno Gause, Heidenhelm (DE)

(73) Assignee: Paul Hartmann AG, Heidenheim (DE)

( * ) Notice: Subject to any disclaimer, the term of this patent is extended or adjusted under 35 U.S.C. 154(b) by 0 days.

(21) Appl. No.: 09/890,316
(22) PCT Filed: Nov. 26, 1999
(86) PCT No.: PCT/EP99/09180
§ 371 (c)(1), (2), (4) Date: Aug. 23, 2001
(87) PCT Pub. No.: WO00/44325
PCT Pub. Date: Aug. 3, 2000

(30) Foreign Application Priority Data

Jan. 28, 1999 (DE) .......................... 199 03 285

(51) Int. Cl.⁷ .......................... A61F 13/15; A61L 15/00
(52) U.S. Cl. .......................... 604/385.02; 604/385.01; 706/440
(58) Field of Search .......................... 604/385.02, 385.04, 604/385.01, 385.03; 206/440, 823; 53/431, 429, 450, 451, 455, 520; 493/186, 189, 243, 960

(56) References Cited

U.S. PATENT DOCUMENTS

| 3,967,729 A | * | 7/1976 | Tanner, II | 206/440 |
| 3,973,567 A | * | 8/1976 | Srinivasan et al. | 604/385.05 |
| 4,556,146 A | | 12/1985 | Swanson et al. | 206/440 |
| 4,564,108 A | | 1/1986 | Widlund | 206/438 |
| 4,605,403 A | | 8/1986 | Tucker | 406/385 |
| 4,735,316 A | | 4/1988 | Froidh et al. | 206/438 |
| 4,857,066 A | * | 8/1989 | Allison | 604/385.13 |
| 5,413,568 A | | 5/1995 | Roach et al. | 604/358 |
| 5,462,166 A | | 10/1995 | Minton et al. | 206/440 |
| 5,474,818 A | | 12/1995 | Ulrich et al. | 428/34 |
| 5,484,636 A | * | 1/1996 | Berg et al. | 428/41.8 |

FOREIGN PATENT DOCUMENTS

| DE | 30 38 364 | 12/1989 |
| EP | 0 750 896 | 1/1997 |
| FR | 2 581 619 | 11/1986 |
| GB | 2 060 398 | 5/1981 |

* cited by examiner

Primary Examiner—Weilun Lo
Assistant Examiner—Jacqueline F Stephens
(74) Attorney, Agent, or Firm—Young & Basile, PC

(57) ABSTRACT

The invention relates to a hygiene article, with an individual wrapping. The wrapping comprises a longitudinal section of a tubular, flatly folded strip provided with a flat side forming an outer side, and which forms an inner side of the wrapping, and having a longitudinal axis parallel to a longitudinal axis of the hygiene article. One longitudinal end is sealed in liquid-tight manner, and the other end is open or can be opened. The hygiene article is laid on the flat inner side of the longitudinal section of the tubular strip, and is folded onto itself together with the longitudinal section around two transversal axes. Longitudinal edges of the longitudinal section are detachably connected to one another to hold the hygiene article in a folded configuration inside the wrapping, to be able to remove the article from the wrapping before use, for disposing of the article, and to be able to insert the same into the open end of the longitudinal section after use.

16 Claims, 4 Drawing Sheets

HYGIENE ARTICLE HAVING AN INDIVIDUAL WRAPPING

DESCRIPTION

The invention relates to a hygiene article, such as an incontinence insert, an insert for briefs or a sanitary napkin, having an individual wrapping.

Hygiene articles having an individual wrapping are known from a large number of publications. U.S. Pat. No. 556,146 describes a sanitary napkin which is placed on a protective cover larger in area and made of fluid-impermeable material and, together with the protective cover, is folded over itself at two transverse axes running perpendicular to the longitudinal axes, whereby the protective cover forms an individual wrapping for the hygiene article. The longitudinal margins of the protective cover which are folded over themselves are attached separately to each other.

It is hardly possible to be able to surround a used hygiene article with the cover layer in such a way that no fluid can escape and also that no offensive odor can arise. A hygiene article is known from U.S. Pat. No. 5,462,166, which is provided with an individual wrapping in a similar fashion. The hygiene article itself, however, is not folded. In this way the particular usable length of a (sheet) forming the wrapper is very long.

U.S. Pat. No. 5,462,166 reveals a comparable individual wrapping, where an adhesive tab is provided in the overlap area of the longitudinal ends of the wrapper to keep the used article in a folded configuration with the wrapper. The problem of fluid escaping at the sides and of offensive odor prove to be a disadvantage.

A hygiene article is known from U.S. Pat. No. 4,735,316 having an individual wrapping, which is formed from a protective cover on which the hygiene article is positioned and which is then folded around the longitudinal edges of the hygiene article on its top side. On the side of the hygiene article facing away from the body, the protective cover has a Z-shaped fold introduced perpendicular to the longitudinal edges, with an inner and an outer fold line running in the longitudinal direction. This is intended to create additional capacity to contain the used hygiene article inside the pocket created by the protective cover. The protective cover thus forms a longitudinal section of a tubular roll, inside which the hygiene article is kept prior to use. Folding the hygiene article together with the individual wrapping in order to save space is neither provided for nor suggested.

In U.S. Pat. No. 4,605,403 a lengthwise section of a tubular roll folded in a Z-shape parallel to its longitudinal axis forms both a cover for a pressure-sensitive adhesive area on the side of a sanitary napkin facing away from the body as well as a disposal pouch for the used sanitary napkin. No provision is made for individual wrapping of the sanitary napkin prior to use.

The object of the present invention is to create a hygiene article having an individual wrapping, which prior to the initial use of the hygiene article provides protection during storage as well as during shipping and subsequent sale of the hygiene article right up to the time of use by the end user, an article which on the one hand saves space with its relatively small surface area and can be carried, for example, in a woman's purse hygienically protected from contamination and whose wrapping on the other hand is suitable for containing the used hygiene article securely, so that no fluid and no odors can escape from the article as it is being carried.

This object is met under the invention by a hygiene article having an individual wrapping prior to initial use during storage as well as during shipping and subsequent sale right up to use by the end user, consisting of a longitudinal section of a tubular smoothly folded roll, with a flat side forming an outer side and an inner side of the individual wrapping, and with a longitudinal axis which runs parallel to a longitudinal axis of the hygiene article, where one longitudinal end of the longitudinal section has a fluid-tight closure and the other end is open or openable, where the hygiene article is placed on the flat side of the longitudinal section of the tubular roll forming the inner side and together with the lengthwise section is folded over itself at two lateral axes running perpendicular to the longitudinal axes, and longitudinal margins folded over themselves are separably attached to each other to keep the hygiene article in the individual wrapping in its folded configuration, so that it can be taken out of its individual wrapping immediately before use, and after being used it can be inserted into the open end of the lengthwise section for disposal of the article.

Under the invention, the individual wrapping is thus formed from a lengthwise section of the tubular roll, onto which the hygiene article is placed and is then, together with the longitudinal section, folded at lateral axes, whereby the individual wrapping is formed. To hold the hygiene article and the individual wrapping in their folded configuration, the longitudinal margins of the longitudinal section, which are folded over each other, are separably attached to each other in such a way that they are kept in a folded configuration prior to initial use, during storage, shipping and sale until immediately before use, but still permit easy opening, i.e. separation of the folded longitudinal margins. The separable attachment can be implemented, for example, by means of adhesive materials which work cohesively or adhesively or by providing a break line, but preferably by thermal embossing. The longitudinal section of the tubular roll thus simultaneously forms the individual wrapping as well as a disposal pouch for the hygiene article without the hygiene article being kept inside the longitudinal section prior to its use and having to be removed in a cumbersome and not very user-friendly manner from the interior of the tubular wrapping for initial use. The disposal pouch has an open end and an end sealed to be fluid-tight, into which the used hygiene article can be inserted and is held and remains there in a fluid-tight manner.

As the result of being folded at two lateral axes, a very compact configuration is achieved for the hygiene article provided in the individual wrapping, and the hygiene article can be carried in a space saving manner, for example, in a woman's purse. In addition, as a result of folding at two lateral axes, in contrast to U.S. Pat. No. 5,474,818, for example, which was mentioned at the beginning, there is a savings in packaging material.

In accordance with a particularly preferred embodiment of the hygiene article, the longitudinal section of the smoothly folded tubular roll comprises two lengths of material arranged on top of each other which form the flat sides of the individual wrapping, which at a distance to their individual longitudinal edges form a fluid-tight and inseparable join with each other in the longitudinal direction. The two lengths of material can for their part be formed from two flat lengths of material which are fed in over each other, which define the tubular roll by being joined together to be fluid-tight and inseparable. But even if the tubular roll is fed in as a single piece, it proves to be advantageous if—as previously mentioned—a fluid-tight and inseparable join is provided on both sides and at a interval to the individual longitudinal edges of the smoothly folded tubular roll, preferably in the form of a seal line, as in such a case the separable join can be provided for the folded longitudinal margins to the outside of this fluid-tight and inseparable join, and when the separable join is opened no leaks can occur in the packaging. In the further development of the invention, the intention is to provide inseparable join lines, which however do not necessarily have to run in a straight line, but can be laid out in a wave or zig-zag shape, and outside of these fluid-tight inseparable join lines, to provide in a lateral direction the separable join for the longitudinal margins of the longitudinal section of the tubular roll which are folded over each other.

In accordance with a further particularly preferred embodiment of the invention, at least one of the lengths of material smoothly folded over each other has a Z-shaped fold along both longitudinal edges, with an inner and an outer fold line running in the longitudinal direction. As a result of this additional step, holding volume can be created for the used hygiene article, without the need for the individual wrapping to have a dimension extending substantially beyond the width of the hygiene article.

In such a case, it is proposed in a further development of this inventive concept that the outer fold lines in the lateral direction are positioned inside the path of the inseparable join between the lengths of material. This makes it possible to provide the inseparable joins between the lengths of material outside the outer fold lines at a time subsequent to the folding, without the Z-shaped fold being touched or affected by this process. Finally, the Z-shaped fold is intended to provide a holding space which can be unfolded, and not be sealed inseparably to one of the lengths of material.

Just the same, an embodiment is also conceivable in which the outer fold lines are not offset to the inside but, for example, run flush with the longitudinal edges of the lengths of material. In such a case, for the fluid-tight inseparable joining of the smoothly folded lengths of material, a dividing metal sheet or similar has to be inserted into the Z-shaped fold, or with the metal folding sheet still inserted, the inseparable join of the lengths of material has to be provided to prevent the fold from being made inseparable. In this case, to prevent the individual wrapping, or the disposal pouch formed from it, from developing a leak in the area of the Z-shaped fold as the result of the separable join or separation of the longitudinal margins, it is recommended that an inner inseparable join be provided quasi as a seal line inside the Z-shaped fold as well. A complex step like this is superfluous however, if—as proposed previously—the Z-shaped fold is carried out in such a way that the outer fold lines in the lateral direction run inside the inseparable join of the lengths of material, and thus also inside the longitudinal margins folded over each other, which are joined separably to each other.

On the outer side facing away from the body, forming the inner side and facing towards the flat side of the longitudinal section of the tubular roll, the hygiene article preferably includes a pressure-sensitive adhesive to attach the article to the crotch of an undergarment. In this instance, the hygiene article can lie directly against the flat side forming the inner side by way of the pressure-sensitive adhesive, as long as it can be detached from it again. In order to be able to reduce the effort required to separate the hygiene article from the flat side of the individual wrapping forming the inside surface, a release coating, for example, in the form of a silicone treatment, can be applied to the inside surface of the individual wrapping.

In accordance with a further variation of this embodiment, the pressure-sensitive adhesive can also be applied on the outside of the hygiene article by means of a release paper. In this case, the hygiene article lies against the inside surface of the individual wrapping, with the release paper located between them. In accordance with a further particularly preferred embodiment, a preferably pressure-sensitive fixative is provided between the release paper and the flat side forming the inside surface. This has the additional advantage that the hygiene article, together with the release paper, can be kept in a predetermined position on the inside surface, which makes it easier to fold the hygiene article at the lateral axes. Secondly, by a suitable choice of difference in the adhesive strengths between the release paper and the pressure-sensitive adhesive on the side of the hygiene article away from the body and between the preferably pressure-sensitive fixative between the release paper and the inside surface of the individual wrapping, when the hygiene article is removed for use, the result is that the release paper remains on the individual wrapping due to the effect of the fixative. The user does not have to dispose of the release paper separately, carry it along or to throw it away, instead it remains on the individual wrapping and is either thrown away immediately along with it, or preferably retained and disposed of along with the used hygiene article after it has been placed in the individual wrapping.

In itself, having only the longitudinal margins, which are folded over each other, attached to each other separably is sufficient to keep the hygiene article in a folded configuration in the individual wrapping. However, it can be advantageous if in addition a preferably pressure-sensitive means of closure is provided, which separably joins the longitudinal ends of the longitudinal section of the tubular roll, which are folded over each other at the two lateral axes. The means of closure can be, for example, strip-shaped tabs which are attached additionally at one longitudinal end of the longitudinal section, or be formed by means of dots of adhesive applied to the inside surface in any given pattern.

The present invention also relates to a method for producing a hygiene article having an individual wrapping of the type previously described, possessing the properties of claim 13, that is to say Feeding a tubular roll or of a first and of a second flat material sheet to form a tubular roll in smoothly folded configuration in a longitudinal direction, inseparable attachment of the smoothly folded lengths of the tubular roll or of the first and second flat material roll on both sides to each other in the longitudinal direction and at a distance to their respective longitudinal edges, successive feeding of hygiene articles in their longitudinal direction parallel to the longitudinal direction of the roll and their positioning on the flat side forming the inside spaced in each case at an interval to each other in the longitudinal direction, Cutting of the tubular roll perpendicular to its longitudinal direction between two hygiene articles placed on it, to create longitudinal sections, Fluid-tight, inseparable join of the smoothly folded sections of each particular longitudinal piece laterally to form a closed longitudinal end on the particular longitudinal section of the tubular roll, Folding the hygiene article over itself together with the longitudinal section the roll at two lateral axes perpendicular to the longitudinal axis, Separable join of longitudinal margins of the particular longitudinal section of the roll which are folded over each other to keep the hygiene article in its folded configuration in the wrapping and to be able to remove it from the individual wrapping for use.

To produce a hygiene article according to the invention, either a single-piece extruded tubular roll without seams, for example, or a single or a first and second sheet of flat material can be fed in to form a tubular roll in the longitudinal direction. In the latter case the sheets of flat material are attached inseparably on both sides to each other to form the tubular roll. In the former case, lengths of the smoothly folded tubular roll which are folded over each other are also fastened inseparably on both sides in the longitudinal direction and at a distance from their respective longitudinal edges. In this way, a longitudinal margin outside of the inseparable join is available to attach the longitudinal margins separably to each other, for example, by thermal embossing, after folding at the lateral axes.

Additional features, details and advantages of the hygiene article having an individual wrapping according to the invention, as well as of the method for its production can be derived from the attached claims, for whose features protection is being claimed independently, and from the illustrations and ensuing description of preferred embodiments of the invention. In the drawings:

Figure 1:
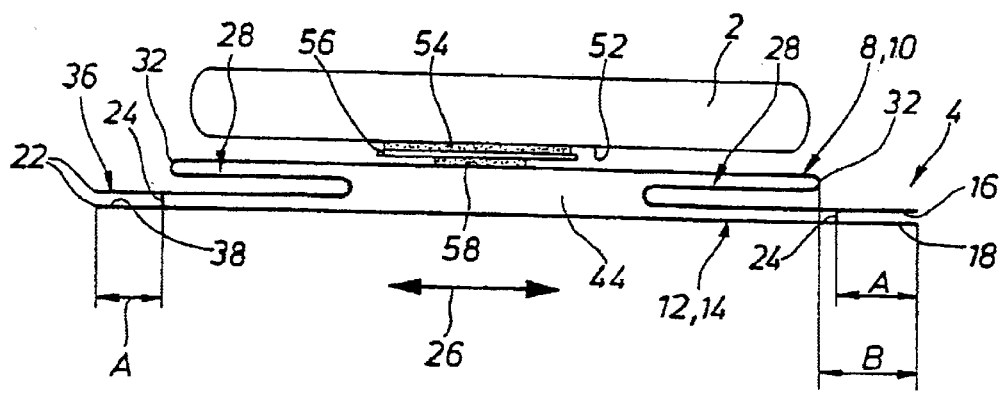
FIG. 1 shows a schematic cross-sectional representation of a hygiene article placed in position on a tubular roll during production.
Figure 2:
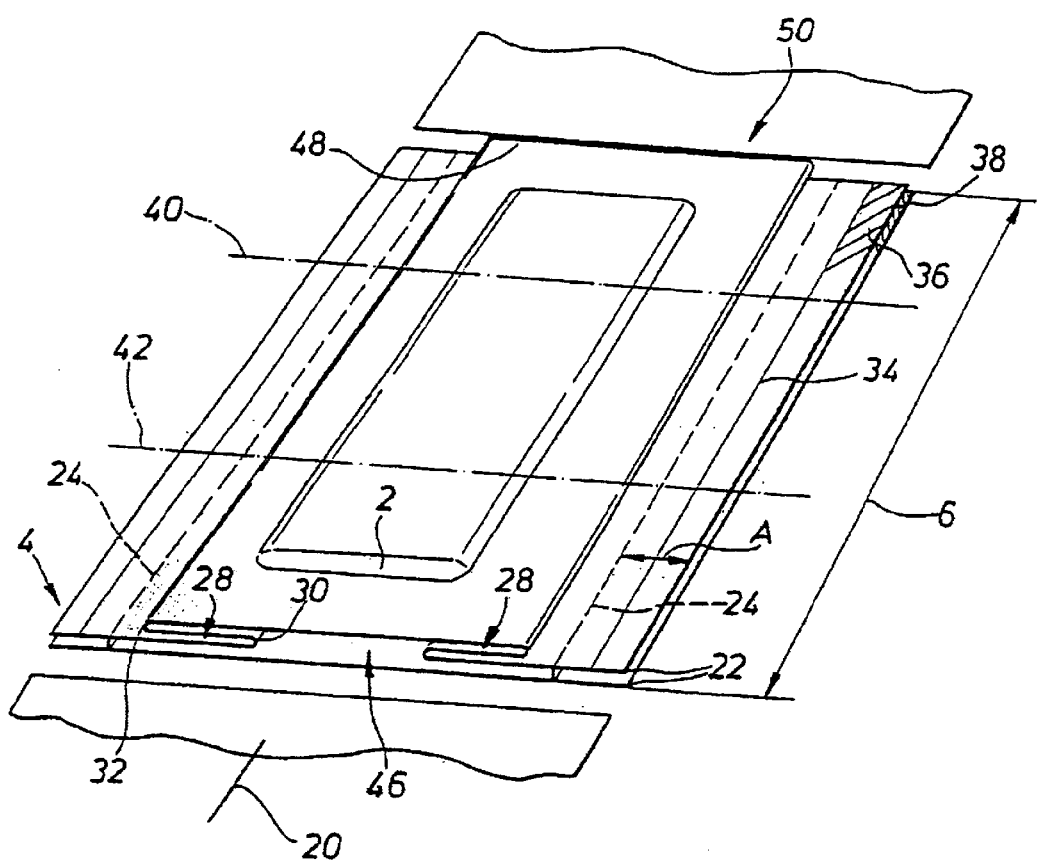
FIG. 2 shows a perspective view of the hygiene article placed in position on the tubular roll.

FIGS. 1 and 2 show a hygiene article 2, indicated only schematically, in the form of an incontinence insert which can be attached to the crotch of an undergarment, placed in position on a tubular roll 4 during an intermediate stage of manufacture.

As will be described subsequently in greater detail, the individual wrapping is formed from a longitudinal section 6 of the tubular roll 4. The longitudinal section 6 of the smoothly folded tubular roll 4 comprises a flat side 10, which forms an inner side 8 of the individual wrapping and a flat side 14 which forms an outer side 12 of the individual wrapping. The flat sides, 10, 14 are sides 16, 18 of lengths of material facing away from each other, which form the tubular roll 4. The lengths of material 16, 18 are joined together in the longitudinal direction 20 and at a distance A from their respective longitudinal edges 22 so as to be fluid-tight and inseparable. This is shown by the join line 24 indicated by the broken line, which is formed by a seal seam running in the longitudinal direction 20.

The upper length of material 16 shown in the drawing which faces the hygiene article 2 includes on both sides of its longitudinal direction 20 a Z-shaped fold 28 introduced in the lateral direction 26, with an inner fold line 30 and an outer fold line 32. The Z-shaped fold 28 was introduced in such a way that the outer fold lines 32 in the lateral direction 26 run inside the inseparable join lines 24 of the lengths of material 16, 18. So they are at distance B from the longitudinal edges 22, which is greater than distance A. This has the advantage that the Z-shaped fold 28 can be introduced first into the sheet of flat material forming the upper length of material 16, and subsequently the permanent join 24 between the lengths of material 16 and 18 can be provided, which does not catch the Z-shaped fold, because it ends up outside the outer fold line 32 in the lateral direction 26.

Figure 3:
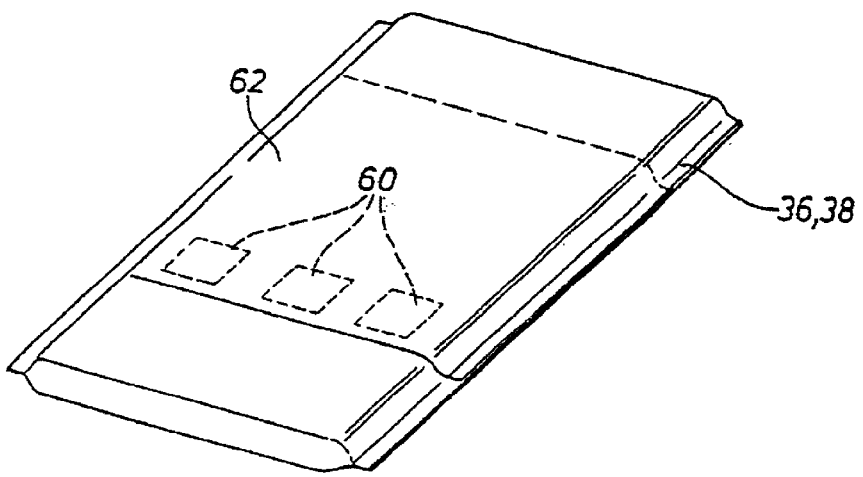
FIG. 3 shows a perspective view of the closed individual wrapping with the hygiene article contained in it, but not shown, for storage, shipping or sale, or for additional storage by stacking.

In FIG. 2 a longitudinal margin 36 of the upper length of material 16 and also a longitudinal margin 38 of the length of material 18 positioned under it is shown by a purely imaginary line 34. These longitudinal margins 36, 38 lie outside the particular fold line 32 and outside the particular line of the permanent, fluid-tight join 24. When a particular longitudinal section 6, after being cut from the tubular roll 4, is folded at two lateral axes 40, 42 together with the hygiene article 2, partial sections of the longitudinal margins 36, 38 are folded over themselves, as is shown in FIG. 3. In order to keep the hygiene article along with its individual wrapping in the folded configuration shown in FIG. 3, the partial sections of the longitudinal margins 36, 38 are joined together separably, preferably by means of thermal embossing. As a result, the longitudinal margins are partially penetrated by the embossing tool. In each case, when the separable join of the particularly grid-like join is separated, damage results to the longitudinal margins 36, 38 of the lengths of material 16, 18. But because the longitudinal margins 36, 38 lie outside the outer fold lines 32 and the line of the permanent join 24, the tightness of the seal inside the lines of the permanent join 24 is not affected. The lower length of material 18 and the upper length of material section 16 with its Z-shaped fold thus define a fluid-tight receiving space 44 and consequently a disposal pouch for the hygiene article after its use. The used hygiene article 2 can then be inserted through an opening 46 into the receiving space. At the opposite end is a fluid-impermeable lateral seam 48, which is formed immediately next to the cut line 50 to detach the longitudinal section 6 from the continuous tubular roll 4.

From FIG. 1 it can also be seen that the hygiene article 2 has a pressure-sensitive adhesive 54 on the side facing away from the body, with which the hygiene article 2 can be attached to the crotch of an undergarment. The pressure-sensitive adhesive applied to the surface is covered by a silicone-treated release paper 56 and is applied over this release paper to the side of the hygiene article 2 facing away from the body 52. Between the release paper 56 and the inside 8 provision is made for a pressure-sensitive fixative 58. The different in adhesive strength between the release paper 56 and the pressure-sensitive adhesive 54 or the pressure-sensitive fixative 58 is such that when the hygiene article 2 is detached from the inside 8 of the individual wrapping, the release paper 56 remains on the inside 8. It should be pointed out that it is also possible to dispense with the release paper, so that the hygiene article 2 lies directly over the pressure-sensitive adhesive 54 against the inside 8 of the individual wrapping. In this case, the adhesive strength against the inside 8 can be set to the desired value by means of an additional release coating on the inside 8 of the individual wrapping, for example, in the form of a silicone treatment.

FIG. 3 shows additional means of closure 60 on the inside of a longitudinal end section 62 of the longitudinal section 6. Overlapping end sections 62 can be attached separably to each other using these means of closure. This proves to be particularly advantageous when the used article is inserted through the opening 46 into the holding space 44 of the disposal bag, and the bag is to be stowed in a space-saving manner because no suitable opportunity for disposal is available. The hygiene article is then folded once more at the lateral axes and kept in its folded configuration by means of the closures 60. The longitudinal margins 36, 38 are folded over each other once more, but generally no provision is made for reclosable means of closure here. Instead of the closures 60 shown as dots of adhesive, an additional tab with an adhesive layer can be provided.

Figure 4A:
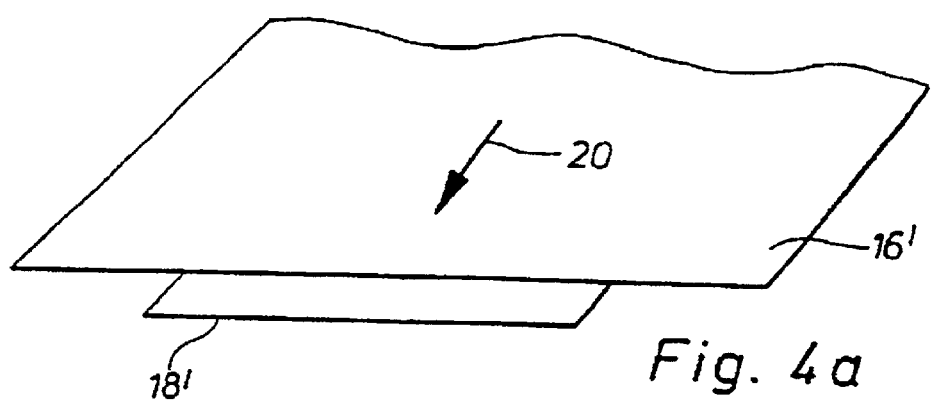
FIGS. 4a–4d show various views of the hygiene article having an individual wrapping during manufacture.
Figure 4B:
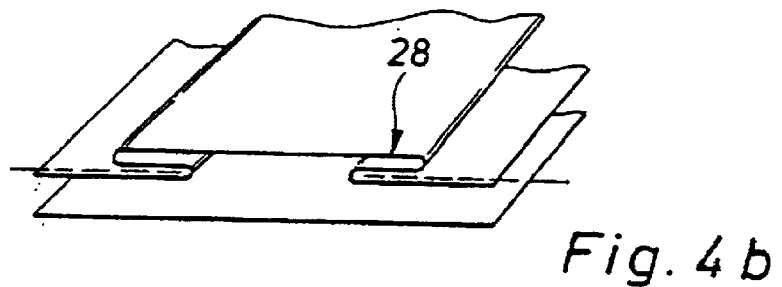

On the basis of FIGS. 4a to 4d a preferred manufacturing method is described for the presently described hygiene article having an individual wrapping. The previously described lengths of material with the reference numerals 16, 18, which form the tubular roll 4, are fed in on top of each other initially in the form of continuous rolls of flat material 16' and 18' in a longitudinal direction 20. Then, using folding irons not shown, the Z-shaped fold 28 is introduced into the upper roll of flat material 16' (FIG. 4b).

Figure 4C:
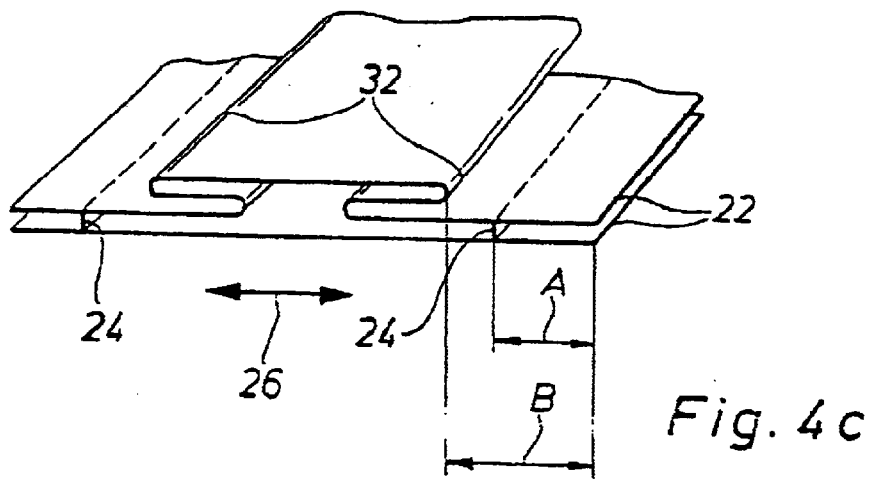
Figure 4D:
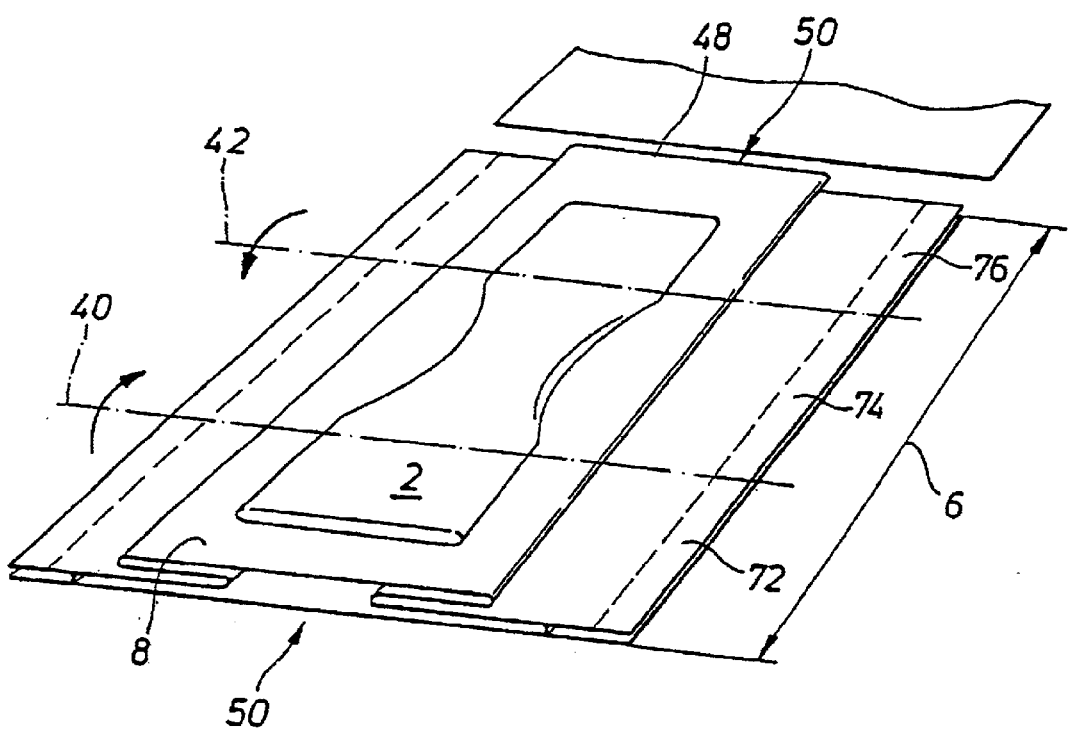

In a further manufacturing step, the rolls of flat material 16', 18' are fastened together permanently in the longitudinal direction 20 and at a distance A from the longitudinal edges 22 by means of a seal seam, which is represented by the join line 24 (FIG. 4c). It must be pointed out that the outer fold line 32 is spaced at a greater distance B from the longitudinal edges 22 than the join line 24. The latter is therefore intended to be outside the outer fold line 32 in the lateral direction 26. Finally, a hygiene article 2 is placed on the inside 8 of the upper roll of flat material 16', and the longitudinal section 6 shown in FIG. 2 is separated from the rolls of material flat 16', 18' along the cut line 50. One end is additionally closed by means of a seal seam 48 running laterally (FIG. 4d).

After separating the longitudinal sections 6 with the hygiene article 2 lying on them, a fold is made in each respective longitudinal section with the hygiene article 2 at the lateral axes 40, 42. To do this, a first partial section 72 of the longitudinal margin 36, 38 is folded onto a center partial section 74 of the longitudinal margin 36, 38, and a third partial section 76 of the longitudinal margin 36, 38 is folded onto the first longitudinal margin 72. So in the overlap area of the longitudinal margin, a total of six layers of the lengths of material 16, 18 are layered over one other. These six layers are attached separably to one other by means of thermal embossing, so that the hygiene article along with its individual wrapping is kept in the configuration shown in FIG. 3 before use. To remove the hygiene article, the separable join in the area of the partial sections 72 to 76 of the longitudinal margin 36, 38 of the respective lengths of material 16, 18 is separated, and the individual wrapping is unfolded along the lateral axes 40, 42, so that the hygiene article 2 can be removed. After the hygiene article has been used, it can be inserted through the open end into the holding space 44 of the disposal bag that has been created in this fashion. Unfolding the z-shaped fold 28 provides adequate holding capacity.

What is claimed is:

1. A hygiene article and an individual wrapping comprising:
    an individual wrapping defining a longitudinal section formed of one of a flattened tubular roll and first and second strips of flat material joined along longitudinal side edges, the longitudinal section having a longitudinal axis;
    the wrapping including a first outer side and an opposed first inner side, and a second outer side and an opposed inner side, the first inner side and the second inner side facing each other to form an interior cavity for the hygiene article after use;
    the longitudinally section having one end is closed in a fluid-tight-manner and one of an open and openable opposite end,
    a hygiene article disposed on the second outer side of the longitudinal section;
    at least two folds formed in the longitudinal section and the hygiene article at two transverse axes substantially perpendicular to the longitudinal axis of the longitudinal section allowing end portions of the longitudinal section and the hygiene article to be folded over; and
    longitudinal margins of the folded end portions of the longitudinal section separably attached to each other.

2. The hygiene article and wrapping in accordance with claim 1, wherein the longitudinal section of the tubular roll comprises two material sections placed over each another forming the flat sides, which are attached inseparably and in a fluid-tight manner to each other at a distance to their respective longitudinal edges in the longitudinal direction.

3. The hygiene article and wrapping in accordance with claim 1, wherein the longitudinal margins of the longitudinal section, which are folded over each other and separably attached, lie outside an inseparable bond of the lengths of material in the lateral direction.

4. The hygiene article and wrapping in accordance with claim 1, wherein the longitudinal margins on the longitudinal section are attached separably by means of thermal embossing.

5. The hygiene article and wrapping in accordance with claim 1, wherein at least one of the lengths of material has at least one Z-shaped fold on at least one of the longitudinal sides with an inner and an outer fold line running in the longitudinal direction.

6. The hygiene article and wrapping in accordance with claim 5, wherein the outer fold lines are located laterally inside a line of an inseparable joining of the lengths of material.

7. The hygiene article and wrapping in accordance with claim 1, wherein the hygiene article on an outside surface facing away from the wrapping has a pressure-sensitive adhesive to attach the hygiene article to an undergarment.

8. The hygiene article and wrapping in accordance with claim 7, wherein by means of a pressure-sensitive adhesive the hygiene article releasably lies directly on the second outer side.

9. The hygiene article and wrapping in accordance with claim 7, wherein the pressure-sersitrve adhesive is applied by means of a release paper to the outside of the hygiene article and the hygiene article, with the release paper interposed, lies against the second outer side.

10. The hygiene article and wrapping in accordance with claim 9, wherein a pressure-sensitive fixative is provided between the release paper and the second outer side to keep the hygiene article in a predetermined position for folding at the lateral axes.

11. The hygiene article and wrapping in accordance with claim 10, wherein the differences in adhesive strength of the release paper to the hygiene article and to the second outer side are set such that the release paper remains on the individual wrapping by means of the fixative when the hygiene article is separated from the wrapping.

12. The hygiene article and wrapping in accordance with claim 1, having a pressure-sensitive closure, which separably joins the two ends of the longitudinal section which are folded over each other at the two lateral axes.

13. A method for manufacturing a hygiene article having an individual wrapping in accordance with claim 1, characterized by the following steps:
    feeding one of a tubular roll and a first and a second strip of flat material to form a tubular roll having a flat configuration in a longitudinal direction;
    inseparable joining folded sections of one of the tubular roll and the first and second flat material strips with each other on both sides in the longitudinal direction and at a distance from respective longitudinal edges to form a first outer side and an opposed first inner side, and a second outer side and an opposed inner side, the first inner side and the second inner side facing each other to form an interior cavity for the hygiene article after use;

successive feeding hygiene articles in the direction of a longitudinal axis parallel to the longitudinal direction of the roll and placement on the second outer side at intervals in the longitudinal direction to each other;

cutting of one of the tubular roll and first and second strips perpendicular to a longitudinal direction between two positioned hygiene articles to form longitudinal sections;

fluid-tight inseparable joining the folded sections of each particular longitudinal section in the lateral direction at one end thereof to create a closed longitudinal end in each respective longitudinal section, folding the hygiene article over on itself together with the longitudinal section at two transverse axes running perpendicular to the longitudinal axis, and releasably joining longitudinal margins of the respective longitudinal section which are folded over on top of each other to removably keep the hygiene article in its folded configuration in the wrapping.

14. The method in accordance with claim 13, wherein the one of the one tubular roll and the first and the second strips of flat material is folded in a Z-shape on both sides around an inner and an outer fold line which runs in the longitudinal direction.

15. The method in accordance with claim 14, wherein the Z-shaped fold is introduced before the inseparable joining of the first and second strips of flat material to each other.

16. The method in accordance with claim 15, wherein the Z-shaped fold is introduced in such a way that an outer fold line is offset towards the inside from the longitudinal edges of the first and second strips of flat material and also runs inside the inseparable fluid-tight joint in the longitudinal direction, so that it is not trapped when the longitudinal margins, which are folded over each other, are inseparably joined together.

* * * * *

UNITED STATES PATENT AND TRADEMARK OFFICE
CERTIFICATE OF CORRECTION

PATENT NO.      : 6,669,676 B1
DATED           : December 30, 2003
INVENTOR(S)     : Enno Gause It is certified that error appears in the above-identified patent and that said Letters Patent is hereby corrected as shown below:

<u>Column 7,</u>
Line 63, delete "longitudinally" and replace with -- longitudinal --.

Signed and Sealed this

Eighteenth Day of May, 2004

JON W. DUDAS
*Acting Director of the United States Patent and Trademark Office*